United States Patent
Pasquier et al.

(10) Patent No.: US 6,749,645 B2
(45) Date of Patent: Jun. 15, 2004

(54) USE OF 4-NITRO-2,1,3,-BENZOXADIAZOLE DERIVATIVES AS DYES IN COLORING AGENTS FOR KERATIN FIBRES

(75) Inventors: Cécile Pasquier, Marly (CH); Véronique Charrière, Courtaman (CH); Hans-Juergen Braun, Ueberstorf (CH)

(73) Assignee: Wella Aktiengesellschaft, Darmstadt (DE)

(*) Notice: Subject to any disclaimer, the term of this patent is extended or adjusted under 35 U.S.C. 154(b) by 130 days.

(21) Appl. No.: 10/089,207

(22) PCT Filed: May 29, 2001

(86) PCT No.: PCT/EP01/07497
§ 371 (c)(1),
(2), (4) Date: Mar. 26, 2002

(87) PCT Pub. No.: WO02/22094
PCT Pub. Date: Mar. 21, 2002

(65) Prior Publication Data
US 2002/0189032 A1 Dec. 19, 2002

(30) Foreign Application Priority Data
Sep. 15, 2000 (DE) .......................... 100 45 599

(51) Int. Cl.$^7$ .............................. A61K 7/13
(52) U.S. Cl. .................. 8/405; 8/437; 8/451; 8/455; 8/462; 548/181
(58) Field of Search ................... 8/405, 437, 451, 8/455, 462; 548/181

(56) References Cited

U.S. PATENT DOCUMENTS

| | | | |
|---|---|---|---|
| 4,620,850 A | 11/1986 | Bachmann | 8/406 |
| 5,055,110 A | 10/1991 | Lim et al. | 8/405 |

FOREIGN PATENT DOCUMENTS

| | | |
|---|---|---|
| DE | 277 678 C | 8/1914 |
| DE | 228 900 A | 10/1985 |
| WO | 01 47485 A | 7/2001 |

OTHER PUBLICATIONS

Journal Fuer Praktische Chemie 327 (3), pp. 487–504, 1985.*
Journal Fuer Praktische Chemie 327 (3), pp. 487–504, 1985.
Analytical Chemistry 1982 (54), pp. 939–942.
Journal of the Chemical Society (B) 1968, pp. 334–338.
Canadian Journal of Chemistry, vol. 75, 1997, pp. 1240–1247.

* cited by examiner

Primary Examiner—Brian P. Mruk
Assistant Examiner—Eisa Elhilo
(74) Attorney, Agent, or Firm—Michael J. Striker

(57) ABSTRACT

The object of the present invention is the use of 4-nitro-2,1,3-benzoxadiazole derivatives of general formula (I) as dye in colorants for keratin fibers such as, for example, wool, silk, furs or hair and particularly human hair

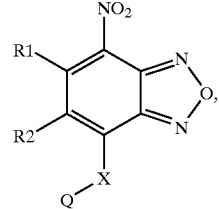

In formula (I)

X denotes oxygen, sulfur or NR$^a$, R$^a$ standing for hydrogen, a (C$_1$–C$_4$)-alkyl group, a monohydroxy-(C$_1$–C$_4$)-alkyl group, a polyhydroxy-(C$_2$–C$_4$)-alkyl group or a mono-(C$_1$ C$_4$)-alkoxy-(C$_1$–C$_4$)-alkyl group, R1 and R2 can be equal or different and independently of each other denote hydrogen, a halogen atom, a (C$_1$–C$_4$)-alkyl group, a halogen-substituted (C$_1$–C$_4$)-alkyl group, a (C$_1$–C$_4$)-alkoxy group, a nitro group or an NR$^b$R$^c$ group, the R$^b$ and R$^c$ groups being equal or different and independently of each other denoting hydrogen, a (C$_1$–C$_4$)-alkyl group, an optionally substituted aromatic carbon ring or a (C$_1$–C$_4$)-alkanecarbonyl group, or R$^b$ and R$^c$ together with the nitrogen atom forming a heterocyclic (C$_3$–C$_6$) group, and Q denotes hydrogen, an aliphatic group, an aromatic isocyclic group or an aromatic heterocyclic group.

11 Claims, No Drawings

USE OF 4-NITRO-2,1,3,-BENZOXADIAZOLE DERIVATIVES AS DYES IN COLORING AGENTS FOR KERATIN FIBRES

BACKGROUND OF THE INVENTION

The present invention relates to colorants for keratin fibers, particularly human hair, containing 4-nitro-2,1,3-benzoxadiazole derivatives as dye.

As a rule, the color-changing treatment of keratin-containing fibers, for example human hair, wool or furs, is carried out by use of two dyeing methods. By the first method, the color is produced with oxidative or permanent colorants by use of a mixture of different developers and couplers and an oxidant. If necessary, to finish the coloring or to create special color effects, direct dyes may be added. The second method makes exclusive use of direct dyes which are applied to the fibers in a suitable carrier composition. This method is simple to use, quite mild and causes only minor damage to the keratin fibers. The direct dyes used for this purpose must meet numerous requirements. They must be toxicologically and dermatologically innocuous and must make it possible to achieve colorations of the desired intensity, which also assumes adequate water solubility, among other things. Moreover, the resulting colorations must be resistant to light, acids and rubbing.

The direct dyes for keratin fibers usually consist of a combination of different nonoxidative dyes. Because the choice of red and blue dyes that can be used in colorants for keratin fibers is limited, a need for such dyes continues to exist.

SUMMARY OF THE INVENTION

The object of the present invention is the use of 4-nitro-2,1,3-benzoxadiazole derivatives of general formula (I) as dye in colorants for keratin fibers, for example wool, silk, furs or hair, particularly human hair,

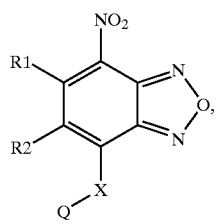

(I)

wherein

X denotes oxygen, sulfur or $NR^a$, $R^a$ standing for hydrogen, a $(C_1-C_4)$-alkyl group, a monohydroxy-$(C_1-C_4)$-alkyl group, a polyhydroxy-$(C_2-C_4)$-alkyl group or a mono-$(C_1-C_4)$-alkoxy-$(C_1-C_4)$-alkyl group, R1 and R2 can be equal or different and independently of each other denote hydrogen, a halogen atom (F, Cl, Br, I), a $(C_1-C_4)$-alkyl group, a halogen-substituted $(C_1-C_4)$-alkyl group, a $(C_1-C_4)$-alkoxy group, a nitro group or an $NR^bR^c$ group, the $R^b$ and $R^c$ groups being equal or different and independently of each other denoting hydrogen, a $(C_1-C_4)$-alkyl group, an optionally substituted aromatic carbon ring or a $(C_1-C_4)$-alkanecarbonyl group, or $R^b$ and $R^c$ together with the nitrogen atom forming a heterocyclic $(C_3-C_6)$ group (for example, an imidazolidino, piperidino, pyrrolidino, pyrazolidino, piperazino or morpholino group);

Q denotes hydrogen, an aliphatic group, an aromatic isocyclic group or an aromatic heterocyclic group, preferably an aromatic monocyclic to tetracyclic group, particularly an aromatic monocyclic or bicyclic group.

DESCRIPTION OF THE PREFERRED EMBODIMENTS

Preferred compounds of formula (I) are those wherein Q has the following meaning: methyl, ethyl, phenyl, biphenyl, $C_6H_4R3$, $C_6H_3R3R4$ or $C_6H_2R3R4R5$ wherein R3, R4 and R5 are equal or different and independently of each other stand for F, Cl, Br, I, CN, $NO_2$, $CF_3$, $(C_1-C_4)$-alkyl, $(C_1-C_4)$-alkoxy, monohydroxy-$(C_1-C_4)$-alkyl polyhydroxy-$(C_2-C_4)$-alkyl, mono-$(C_1-C_4)$-alkoxy-$(C_1-C_4)$-alkyl, $(C_1-C_4)$-alkylthio, hydroxy $NR^dR^e$, CHO, $COR^f$, COOH, $COOR^g$, $CONHR^h$ or $NHCOR^i$, wherein $R^d$ and $R^e$ independently of each other denote hydrogen, a $(C_1-C_4)$-alkyl group, a monohydroxy-$C_1-C_4$-alkyl group, a polyhydroxy-$(C_2-C_4)$-alkyl group or an optionally substituted aromatic carbon ring, and $R^f$, $R^g$, $R^h$ and $R^i$ independently of each other denote a $(C_1-C_4)$-alkyl group or an optionally substituted aromatic carbon ring.

Particularly preferred among the abovesaid compounds of formula (I) are those wherein: X stands for oxygen or $NR^a$, with $R^a$ denoting hydrogen, a $(C_1-C_4)$-alkyl group, a monohydroxy-$(C_1-C_4)$-alkyl group, a polyhydroxy-$(C_2-C_4)$-alkyl group or a mono-$(C_1-C_4)$-alkoxy-$(C_1-C_4)$-alkyl group;

R1=R2=hydrogen; Q stands for methyl, ethyl, phenyl, biphenyl, $C_6H_4R3$, $C_6H_3R3R4$ or $C_6H_2R3R4R5$, wherein R3, R4 and R5 are equal or different and independently of each other stand for F, Cl, Br, I, CN, $NO_2$, $CF_3$, $(C_1-C_4)$-alkyl, $(C_1-C_4)$-alkoxy, monohydroxy-$(C_1-C_4)$-alkyl, polyhydroxy-$(C_2-C_4)$-alkyl, mono-$(C_1-C_4)$-alkoxy-$(C_1-C_4)$-alkyl, $(C_1-C_4)$-alkylthio, hydroxy, $NR^dR^e$, CHO, $COR^f$, COOH, $COOR^g$, $CONHR^h$ or $NHCOR^i$ wherein $R^d$ and $R^e$ independently of each other denote hydrogen, a $(C_1-C_4)$-alkyl group, a monohydroxy-$(C_1-C_4)$-alkyl group, a polyhydroxy-$(C_2-C_4)$-alkyl group or an optionally substituted aromatic carbon ring, and $R^f$, $R^g$, $R^h$ and $R^i$ independently of each other denote a $(C_1-C_4)$-alkyl group or an optionally substituted aromatic carbon ring.

Suitable 4-nitro-2,1,3-benzoxadiazole derivatives of formula (I) are, for example: 4-amino-7-nitro-2,1,3-benzoxadiazole; 4-N,N-dimethylamino-7-nitro-2,1,3-benzoxadiazole; 4-nitro-7-methoxy-2,1,3-benzoxadiazole; 4-nitro-7-ethoxy-2,1,3-benzoxadiazole; 4-nitro-7-phenoxy-2,1,3-benzoxadiazole; 4-nitro-7-(4'-nitrophenoxy)-2,1,3-benzoxadiazole; 4-nitro-7-(2',4',6'-trimethylphenoxy)-2,1,3-benzoxadiazole; 7-nitro-4-(N-phenylamino)-2,1,3-benzoxadiazole; 4-[N-1-(naphthalenyl)amino]-7-nitro-2,1,3-benzoxadiazole; 4-[N-(4'-chlorophenyl)amino]-7-nitro-2,1,3-benzoxadiazole; 4-[N-(4'-fluorophenyl)amino]-7-nitro-2,1,3-benzoxadiazole; 7-nitro-4-[N-(4'-nitrophenyl)amino]-2,1,3-benzoxadiazole; 7-nitro-4-[N-(3'-nitrophenyl)amino]-2,1,3-benzoxadiazole; 4-[N-(2',4'-dinitrophenyl)amino]-7-nitro-2,1,3-benzoxadiazole; 4-[(7-nitro-2,1,3-benzoxadiazol-4-yl)amino]benzonitrile; 4-[N-(4'-methylphenyl)amino]-7-nitro-2,1,3-benzoxadiazole; 4-[N-(2'-methylphenyl)amino]-7-nitro-2,1,3-benzoxadiazole; 4-[N-(4'-methoxyphenyl)amino]-7-nitro-2,1,3-benzoxadiazole; 4-[(7-nitro-2,1,3-benzoxadiazol-4-yl)amino]phenol; 4-[(7-nitro-2,1,3-benzoxadiazol-4-yl)amino]-3-chloro-5-nitrophenol; 3-[(7-nitro-2,1,3-benzoxadiazol-4-yl)amino]phenol; 2-[(7-nitro-2,1,3- benzoxadiazol-4-yl)amino]phenol; N-(7-nitro-2,1,3-benzoxadiazol-4-yl)-1,4-diaminobenzene; N,N-dimethyl-N'-(7-nitro-2,1,3-benzoxadiazol-4-yl)-1,4-diaminobenzene; N-(7-nitro-2,1,3-benzoxadiazol-4-yl)-2-(2'-hydroxyethyl)-1,4-diaminobenzene; N-(7-nitro-2,1,3-benzoxadiazol-4-yl)-2-(1'-hydroxyethyl)-1,4-diaminobenzene; N-(7-nitro-2,1,3-benzoxadiazol-4-yl)-2-methoxymethyl-1,4-diaminobenzene; N,N-di-(2'-hydroxyethyl)-N'-(7-nitro-2,1,3-benzoxadiazol-4-yl)-2-nitro-1,4-diaminobenzene; methyl 4-[(7-nitro-2,1,3-benzoxadiazol-4-yl)amino]benzoate; 4-nitro-7-(phenylthio)-2,1,3-benzoxadiazole; 4-[(4'-chlorophenyl)thio]-7-nitro-2,1,3-benzoxadiazole; 4-[(3'-chlorophenyl)thio]-7-nitro-2,1,3-benzoxadiazole; 4-[(4'-bromophenyl)thio]-7-nitro-2,1,3-benzoxadiazole; 4-[(4'-methylphenyl)thio]-7-nitro-2,1,3-benzoxadiazole; 4-[(3'-methoxyphenyl)thio]-7-nitro-2,1,3-benzoxadiazole; 4-nitro-7-[(4'-nitrophenyl)thio]-2,1,3-benzoxadiazole; 2-[(7-nitro-2,1,3-benzoxadiazol-4-yl)thio]benzoic acid; 5,7-dinitro-N-phenyl-4-amino-2,1,3-benzoxadiazole; 4-{N-[(1,1'-biphenyl)-4-yl]amino}-5,7-dinitro-2,1,3-benzoxadiazole; 4-[N-(4'-chlorophenyl)amino]-5,7-dinitro-2,1,3-benzoxadiazole; 4-[N-(4'-bromophenyl)amino]-5,7-dinitro-2,1,3-benzoxadiazole; 4-[N-(3'-bromophenyl)amino]-5,7-dinitro-2,1,3-benzoxadiazole; 5,7-dinitro-4-[N-(4'-nitrophenyl)amino]-2,1,3-benzoxadiazole; 5,7-dinitro-4-[N-(3'-nitrophenyl)amino]-2,1,3-benzoxadiazole; 4-[N-(4'-methoxyphenyl)amino]-5,7-dinitro-2,1,3-benzoxadiazole; 4-[N-(4'-methylphenyl)amino]-5,7-dinitro-2,1,3-benzoxadiazole; N'-(5,7-dinitro-2,1,3-benzoxadiazol-4-yl)-N,N-dimethyl-1,4-diaminobenzene; 3-[(5,7-dinitro-2,1,3-benzoxadiazol-4-yl)amino]phenol; 4-(N-methyl-N-phenylamino)-7-nitro-2,1,3-benzoxadiazole or 4-(N-ethyl-N-phenylamino)-7-nitro-2,1,3-benzoxadiazole and 4-[N-(2'-hydroxyethyl)-N-[4-di-(2'-hydroxyethyl)-2-nitrophenylamino]-7-nitro-2,1,3-benzoxadiazole.

The following among the aforesaid compounds of formula (I) are particularly preferred: 4-nitro-7-methoxy-2,1,3-benzoxadiazole; 4-nitro-7-ethoxy-2,1,3-benzoxadiazole; 4-nitro-7-phenoxy-2,1,3-benzoxadiazole; 7-nitro-4-(N-phenylamino)-2,1,3-benzoxadiazole; 4-[N-4'-methylphenyl)amino]-7-nitro-2,1,3-benzoxadiazole; 4-[N-4'-methoxyphenyl)amino]-7-nitro-2,1,3-benzoxadiazole; 4-[(7-nitro-2,1,3-benzoxadiazol-4-yl)amino]phenol; 3-[(7-nitro-2,1,3-benzoxadiazol-4-yl)amino]phenol; 2-[(7-nitro-2,1,3-benzoxadiazol-4-yl)amino]phenol; 4-[(7-nitro-2,1,3-benzoxadiazol-4-yl)amino]-3-chloro-5-nitrophenol; N-(7-nitro-2,1,3-benzoxadiazol-4-yl)-1,4-diaminobenzene; N-(7-nitro-2,1,3-benzoxadiazol-4-yl)-2-(2'-hydroxyethyl)-1,4-diaminobenzene; N-(7-nitro-2,1,3-benzoxadiazol-4-yl)-2-(1'-hydroxyethyl)-1,4-diaminobenzene; N-(7-nitro-2,1,3-benzoxadiazol-4-yl)-2-(methoxymethyl)-1,4-diaminobenzene; N,N-dimethyl-N'-(7-nitro-2,1,3-benzoxadiazol-4-yl)-1,4-diaminobenzene; N,N-di-(2'-hydroxyethyl)-N'-(7-nitro-2,1,3-benzoxadiazol-4-yl)-2-nitro-1,4-diaminobenzene and 4-(N-(2'-hydroxyethyl-N-[4-di-(2'-hydroxyethyl)-2-nitrophenylamino]-7-nitro-2,1,3-benzoxadiazole.

The 4-nitro-2,1,3-benzoxadiazole derivatives of formula (I) are usually employed in the form of a conventional colorant, the compound of formula (I) preferably being used in an amount from about 0.01 to about 10 wt. % and particularly from about 0.1 to about 8 wt. %.

Depending on the desired color shade, the colorant can optionally also contain, besides the dyes of formula (I), other known direct dyes from the group of anionic or cationic dyes, nitro dyes, azo dyes, anthraquinone dyes, triphenylmethane dyes or disperse dyes, it being possible to use said dyes individually or in admixture with each other.

In the colorants of the invention, the aforesaid direct dyes can be used in a total amount of about 0.01 to about 4 wt. %, the total amount of dyes in the colorant of the invention preferably being from about 0.01 to about 10 wt. % and particularly from about 0.1 to about 5 wt. %.

In addition, the colorants can contain all known and common additives for such preparations, for example perfume oils, complexing agents, waxes, preservatives, thickeners, alginates, guar gum, hair-care substances such as, for example, cationic polymers or lanolin derivatives, or anionic, nonionic, amphoteric or cationic surface-active substances. Preferably used are amphoteric or nonionic surface-active substances, for example betaine surfactants, propionates and glycinates such as, for example, cocoamphoglycinates or cocamphodiglycinates, ethoxylated surfactants with 1 to 1000 ethylene oxide units, preferably with 1 to 300 ethylene oxide units, for example glyceride alkoxylates, for example castor oil ethoxylated with 25 ethylene oxide units, polyglycolamides, ethoxylated alcohols and ethoxylated fatty alcohols (fatty alcohol alkoxylates) and ethoxylated fatty acid esters of sugars, particularly ethoxylated sorbitan fatty acid esters. The aforesaid constituents are used in amounts commonly employed for such purposes, for example the surface-active substances at a concentration from 0.1 to 30 wt. % and the hair-care agents in an amount from 0.1 to 5 wt. %.

Besides water, the colorants can also contain organic solvents, for example aliphatic or aromatic alcohols such as, for example, ethanol, isopropanol, 1,2-propanediol, 1-methoxypropan-2-ol, 1-ethoxypropan-2-ol, diethylene glycol monomethyl ether or diethylene glycol monoethyl ether, dipropylene glycol monomethyl ether, dipropylene glycol monoethyl ether, benzyl alcohol, benzyloxyethanol, phenylethyl alcohol, phenoxyethanol, cinnamyl alcohol and glycol ethers, particularly ethanol, isopropanol or benzyl alcohol. The water content is usually from about 25 to about 95 wt. % and preferably from about 30 to about 85 wt. %, whereas the organic solvent or solvent mixture is present in an amount from about 5 to about 30 wt. %.

The colorant, particularly when it is a hair colorant, can be in the form of an aqueous or aqueous-alcoholic solution, a cream, a gel, an emulsion or an aerosol foam. The hair colorant is packaged in the form of either a one-component preparation or a multicomponent preparation, for example in the form of a two-component preparation. In the latter case, the dye derivative of formula (I) is packaged separately from the other components, and the ready-for-use hair colorant is prepared only just before use by mixing the two components.

The colorant has a pH from about 3 to about 10 and preferably from about 4 to about 10. Both organic and inorganic acid and bases can be used for pH adjustment.

Suitable acids are, in particular, the following: α-hydroxycarboxylic acids, for example glycolic acid, lactic acid, tartaric acid, citric acid or malic acid; ascorbic acid; gluconolactone; acetic acid; hydrochloric acid or phosphoric acid, as well as mixtures of said acids.

Suitable bases are, in particular, sodium carbonate, sodium hydrogen carbonate, potassium carbonate, potassium hydrogen carbonate, sodium phosphate, borax ($Na_2B_4O_7 \cdot 10H_2O$), disodium hydrogen phosphate, alkanolamines, for example monoethanolamine or triethanolamine, ammonia, aminomethylpropanol and sodium hydroxide.

As a rule, the colorant is used by applying to the hair an amount sufficient for hair dyeing, namely about 30 to about 120 grams, depending on the length of the hair, allowing the colorant to act for about 1 to about 60 min, preferably 5 to 30 min, at about 15 to about 45° C., then rinsing the hair thoroughly with water, optionally washing it with a shampoo and finally drying it.

The colorant described in the foregoing also contains natural or synthetic polymers or modified polymers of natural origin commonly used in cosmetic preparations so that the hair is fixed at the same time it is being colored. In general, such agents are referred to as shade fixatives or color fixatives.

Suitable among the known synthetic polymers used for this purpose in cosmetics are, for example, polyvinylpyrrolidone, polyvinyl acetate, polyvinyl alcohol or polyacrylic compounds such as polyacrylic acid, polymethacrylic acid, basic polymers of esters of polyacrylic acid or polymethacrylic acid and aminoalcohols, for example the salts or quaternized products thereof, polyacrylonitrile, polyvinyl acetates and the copolymers of such compounds, for example polyvinylpyrrolidone-vinyl acetate. Suitable natural polymers or modified natural polymers are, for example, chitosan (deacetylated chitin) or chitosan derivatives.

The aforesaid polymers can be contained in the colorant in amounts commonly used for such preparations, particularly in an amount from about 1 to about 5 wt. %. The pH of the shade fixative or color fixative is preferably from about 6 to about 9.

The colorant and the additional fixing are carried out in the usual manner by moistening the hair with the fixative, styling and setting the hair and then drying.

The colorants containing the 4-nitro-2,1,3-benzoxadiazole derivatives of general formula (I) impart to keratin fibers (particularly human hair) under gentle, skin-compatible conditions an outstanding, uniform, intense and long-lasting coloration that is highly resistant to shampooing, light and perspiration.

Because of their high resistance to oxidants, the 4-nitro-2,1,3-benzoxadiazole derivatives of general formula (I) can also be used in oxidative colorants based on oxidation dye precursors. The 4-nitro-2,1,3-benzoxadiazole derivatives of general formula (I) can also be used in brightening shades wherein—for purposes of brightening or improving the luster of the hair to be colored—the direct dyes are used in combination with an oxidant.

The 4-nitro-2,1,3-benzoxadiazole derivatives of general formula (I) can be prepared by introducing substituents into 4-nitro-2,1,3-benzoxadiazoles of formula (II) [wherein Y denotes halogen or $OCH_3$ or $OCH_2CH_3$, and R1 and R2 have the same meaning as in formula (I)] by means of amines, alcohols, phenols, thioalcohols or thiophenols.

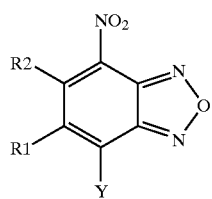

(II)

General methods of preparation are described in the literature, for example in E. German Patent 227 704; Journal für praktische Chemie 327 (3), pages 487–504 (1985); Analytical Chemistry 1982 (54), pages 939–942; Journal of the Chemical Society (B) 1968, pages 334–338 or Canadian Journal of Chemistry, vol. 75 (1997), pages 1240–1247.

The following examples illustrate the object of the invention in greater detail without limiting its scope.

EXAMPLES

Example 1

Synthesis of 7-nitro-4-(N-phenylamino)-2,1,3-benzoxadiazole 4 g (20 mmoles) of 4-chloro-7-nitro 2,1,3-benzoxadiazole (NBD-Cl) was suspended in 100 mL of ethanol. To the suspension was added 1.7 g (20 mmoles) of sodium hydrogen carbonate. To the reaction mixture was added dropwise 1.9 g (20 mmoles) of aniline at room temperature (20–25° C.). The mixture was allowed to agitate 2 hours at room temperature and then an additional hour at 50° C. At the end of the reaction, the reaction mixture was poured onto 600 mL of water/ice. The precipitated product was filtered off, washed with water and then dried.

The yield was 93% of the theoretical.

Melting point: 152–153° C. $ESI^1$ mass spectrum: $M^+$-1: 255 (100% rel. intensity). $^1$H-NMR (DMSO): 11.06 (s, 1H, NH); 8.55 [d, J=9 Hz, 1H, H—C (6)]; 7.56–7.48 [m, 4H); 7.3–7.32 (m, 1H); 6.73 [d, J=9 Hz, 1H, H—C (5)]. UV-VIS spectrum (EtOH): $\lambda_{max}$=472 nm (23410) Elemental analysis: $C_{12}H_8N_4O_3$ (256.22)

|  | % C | % H | % N |
|---|---|---|---|
| Calcd.: | 56.25 | 3.15 | 21.87 |
| Found: | 56.50 | 3.13 | 22.18 |

Example 2

Synthesis of N-(7-nitro-2,1,3-benzoxadiazol-4-yl)-1,4-diaminobenzene 2 g (10 mmoles) of 4-chloro-7-nitro 2,1,3-benzoxadiazole (NBD-Cl) was suspended in 30 mL of ethanol. To the suspension was added 0.84 g (10 mmoles) of sodium hydrogen carbonate. To the reaction mixture was added dropwise 1.1 g (10 mmoles) of 1,4-diaminobenzene at room temperature (20–25° C.) and the mixture was allowed to agitate for 3 hours at room temperature. At the end of the reaction, the reaction mixture was poured onto 250 mL of water/ice and the precipitated product was filtered off, washed with water and then dried.

The yield was 94% of the theoretical.

Melting point: 205–207° C. ESI mass spectrum: $M^+$-1: 270 (100% rel. intensity). $^1$H-NMR (DMSO): 10.94 (s, 1H, NH); 8.49 [d, J=9 Hz, 1H, H—C (6)]; 7.15–7.10 [m, 2H); 6.70–7.65 (m, 2H); 6.50 [d, J=9 Hz, 1H, H—C (5)]; 5.46 (br s, 2H, $NH_2$). UV-VIS spectrum (EtOH): $\lambda_{max}$=488 nm (17120) Elemental analysis: $C_{12}H_9N_5O_3$ (271.24)

|  | % C | % H | % N |
|---|---|---|---|
| Calcd.: | 53.14 | 3.34 | 25.82 |
| Found: | 52.74 | 3.29 | 25.82 |

Example 3

Synthesis of N-(7-nitro-2,1,3-benzoxadiazol-4-yl)-2-(2'-hydroxyethyl)-1,4-diaminobenzene 1 g (5 mmoles) of 4-chloro-7-nitro 2,1,3-benzoxadiazole (NBD-Cl) was suspended in 25 mL of ethanol. To the suspension was added 1.3 g (15 mmoles) of sodium hydrogen carbonate. To the reaction mixture was added dropwise 2 g (5 mmoles) of 1,4-diamino-2-(2'-hydroxyethyl)benzene sulfate at room temperature (20–25° C.). The mixture was allowed to agitate for about 2.5 hours at room temperature. At the end of the reaction, the reaction mixture was poured onto 300 mL of water/ice and the precipitated product was filtered off, washed with water and then dried.

The yield was 82% of the theoretical.

Melting point: 200–202° C. ESI mass spectrum: $M^+$−1: 314 (100% rel. intensity). $^1$H-NMR (DMSO): 10.94 (s, 1H, NH); 8.47 [d, J=9 Hz, 1H, H—C (6)]; 7.07–7.01 [m, 2H]; 6.73 (d, J=8.5, 1H); 6.52 [d, J=9 Hz, 1H, H—C (5)]; 5.33 (br s, 2H, $NH_2$); 4.69 (br s, 1H OH); 3.64 (t, J=6.6 Hz, 2H, $CH_2OH$); 2.64 (t, J=6.6 Hz, 2H, $CH_2$). UV-VIS spectrum (EtOH): $\lambda_{max}$=490 nm (18125) Elemental analysis: $C_{14}H_{13}N_5O_4$ (315.29)

|  | % C | % H | % N |
| --- | --- | --- | --- |
| Calcd.: | 53.33 | 4.16 | 22.21 |
| Found: | 53.00 | 4.12 | 22.12 |

Example 4

Synthesis of 4-[(7-nitro-2,1,3-benzoxadiazol-4-yl)amino]phenol 4 g (20 mmoles) of 4-chloro-7-nitro 2,1,3-benzoxadiazole (NBD-Cl) was suspended in 100 mL of ethanol. To the suspension was added 1.7 g (20 mmoles) of sodium hydrogen carbonate. To the reaction mixture was added dropwise 2.2 g (20 mmoles) of 4-aminophenol at room temperature (20–25° C.). The mixture was allowed to agitate for about 3 hours at room temperature. At the end of the reaction, the reaction mixture was poured onto 500 mL of water/ice and the precipitated product was filtered off, washed with water and then dried.

The yield was 95% of the theoretical.

Melting point: 215–216° C. ESI mass spectrum: $M^+$−1: 271 (100% rel. intensity). $^1$H-NMR (DMSO): 10.96 (s, 1H, NH); 9.76 (s, 1H, OH); 8.51 [d, J=9 Hz, 1H, H—C (6)]; 7.31–7.26 [m, 2H); 6.92–6.87 (m, 2H); 6.51 [d, J=9 Hz, 1H), H—C (5)]. UV-VIS spectrum (EtOH): $\lambda_{max}$=482 nm (14160) Elemental analysis: $C_{12}H_8N_4O_4$ (272.22)

|  | % C | % H | % N |
| --- | --- | --- | --- |
| Calcd.: | 52.95 | 2.96 | 20.58 |
| Found: | 52.51 | 2.81 | 20.49 |

Example 5

Synthesis of 4-nitro-7-phenoxy-2,1,3-benzoxadiazole 1 g (5 mmoles) of 4-chloro-7-nitro 2,1,3-benzoxadiazole (NBD-Cl) was suspended in 20 mL of ethanol. To the suspension was added 0.2 g (5 mmoles) of sodium hydroxide. To the reaction mixture was added dropwise 0.47 g (5 mmoles) of phenol at room temperature (20–25° C.). The mixture was allowed to agitate 24 hours at room temperature and then poured onto 200 mL of water/ice. The resulting mixture was extracted several times with ethyl acetate. The combined organic phases were washed with NaCl solution, dried over $MgSO_4$, filtered and concentrated. The resulting product was recrystallized from ethanol.

The yield was 38% of the theoretical.

Melting point: 114–116° C. ESI mass spectrum: $M^+$+Na: 280 (100% rel. intensity). $^1$H-NMR (DMSO): 8.67 [d, J=9 Hz, 1H, H—C (6)]; 7.66–7.59 [m, 2H); 7.48–7.42 (m, 2H); 6.70 [d, J=9 Hz, 1H, H—C (5)]. UV-VIS spectrum (EtOH): $\lambda_{max}$=370 nm (11100) Elemental analysis: $C_{12}H_7N_3O_4$ (257.20)

|  | % C | % H | % N |
| --- | --- | --- | --- |
| Calcd.: | 56.04 | 2.74 | 16.34 |
| Found: | 55.70 | 2.84 | 16.24 |

Example 6

Synthesis of 4-nitro-7-methoxy-2,1,3-benzoxadiazole 2 g (10 mmoles) of 4-chloro-7-nitro 2,1,3-benzoxadiazole (NBD-Cl) was suspended in 20 mL of anhydrous methanol. The reaction mixture was cooled to 5° C. and to it was added dropwise 0.63 g (11 mmoles) of sodium methoxide at this temperature. The reaction mixture was then warmed up to room temperature. After a 20-hour agitation period at room temperature, the precipitated product was filtered off, washed with cold methanol and then dried.

The yield was 45% of the theoretical.

Melting point: 116–118° C. ESI mass spectrum: $M^+$+Na: 218 (100% rel. intensity). $^1$H-NMR (DMSO): 8.77 [d, J=8.4 Hz, 1H, H—C (6)]; 7.08 [d, J=8.4 Hz, 1H, H—C (5)]; 4.22 (s, 3H, $CH_3$). UV-VIS spectrum (EtOH): $\lambda_{max}$=370 nm (11200) Elemental analysis: $C_7H_5N_3O_4$ (195.13)

|  | % C | % H | % N |
| --- | --- | --- | --- |
| Calcd.: | 43.09 | 2.58 | 21.53 |
| Found: | 43.08 | 2.48 | 21.32 |

Examples 7 to 12

Colorants in Solution 2.5 mmoles of dye of formula (I) according to Table 1
5.0 g of ethanol
4.0 g of decyl polyglucoside (aqueous solution; Plantaren® 2000, supplied by Cognis, Germany)
0.2 g of disodium ethylenediaminetetraacetate hydrate
to 100.0 g water, demineralized By addition of ammonia or citric acid, the colorant solution was adjusted to pH 10 (Examples 7 to 10) or pH 7.5 (Examples 11 and 12).

The coloring of the hair was carried out by applying to bleached hair an amount of colorant sufficient for hair dyeing. After an exposure time of 30 min at 40° C., the hair was rinsed with luke-warm water and dried.

The coloring results are summarized in the following Table 1.

TABLE 1

| Example No./Dye of Formula (I) | Color | L * a * b * Color Values |
|---|---|---|
| 7 7-nitro-4-(N-phenylamino)-2,1,3-benzoxadiazole (from Example 1) | bright orange | L = +59.72<br>a = +42.22<br>b = +66.23 |
| 8 N-(7-nitro-2,1,3-benzoxadiazol-4-yl)-1,4-diaminobenzene (from Example 2) | violet | L = +27.57<br>a = +27.27<br>b = +3.22 |
| 9 N-(7-nitro-2,1,3-benzoxadiazol-4-yl)-2-(2'-hydroxyethyl)-1,4-diaminobenzene (from Example 3) | violet | L = +26.45<br>a = +24.53<br>b = +1.06 |
| 10 4-[(7-nitro-2,1,3-benzoxadiazol-4-yl-amino]phenol (from Example 4) | ruby-red | L = +25.63<br>a = +41.77<br>b = +16.83 |
| 11 4-nitro-7-phenoxy-2,1,3-benzoxadiazole (from Example 5) | yellow | L = +78.24<br>a = −1.66<br>b = +51.02 |
| 12 4-nitro-7-ethoxy-2,1,3-benzoxadiazole (from Example 6) | golden-yellow | L = +72.53<br>a = +6.95<br>b = +90.12 |

Examples 13 to 15

Colorants in Cream Form 2.5 mmoles of dye of formula (I) according to Table 2
12 g of cetylstearyl alcohol
10 g of lauryl ether sulfate, 28% aqueous solution
20 g of ethanol
to 100.0 g water, demineralized The cetylstearyl alcohol was melted at 80° C. Lauryl ether sulfate, heated to 80° C. together with 95% of the water, was then added, and the mass was stirred until a cream was formed. The dye, the ethanol and the remainder of the water were added at room temperature, and the pH was adjusted to 9.5 by adding ammonia.

The hair was dyed by applying to bleached hair an amount of hair-dyeing cream sufficient for this purpose. After an exposure time of 30 min at 40° C., the hair was rinsed with luke-warm water, washed with a shampoo, again rinsed with luke-warm water and then dried.

The coloring results are summarized in the following Table 2.

TABLE 2

| Example No./Dye of Formula (I) | Color | L * a * b * Color Values |
|---|---|---|
| 13 7-nitro-4-(N-phenylamino)-2,1,3-benzoxadiazole (from Example 1) | bright orange | L = +59.10<br>a = +42.70<br>b = +66.60 |
| 14 N-(7-nitro-2,1,3-benzoxadiazol-4-yl)-1,4-diaminobenzene (from Example 2) | violet | L = +24.30<br>a = +25.40<br>b = +2.10 |
| 15 4-[(7-nitro-2,1,3-benzoxadiazol-4-yl)amino]phenol (from Example 4) | ruby-red | L = +23.40<br>a = +37.50<br>b = +13.30 |

Examples 16 and 17

Hair Colorants in the Presence of Hydrogen Peroxide 5.0 mmoles of dye of formula (I) according to Table 3
10.0 g of lauryl ether sulfate (28% aqueous solution)
7.8 g of ethanol
0.3 g of ascorbic acid
0.3 g of disodium ethylenediaminetetraacetate hydrate
9.0 g of ammonia (22% aqueous solution)
to 100.0 g water, demineralized Just before use, 4 g of the foregoing dye solution was mixed with 4 g of a 6% hydrogen peroxide solution. The pH of the mixture was 9.6.

The mixture was then applied to bleached buffalo hair. After an exposure time of 30 min at 40° C., the hair was rinsed with luke-warm water and dried. The coloring results are summarized in Table 3.

TABLE 3

| Example No./Dye of Formula (I) | Color | L * a * b * Color Values |
|---|---|---|
| 16 N-(7-nitro-2,1,3-benzoxadiazol-4-yl)-1,4-diaminobenzene (from Example 2) | violet | L = +26.68<br>a = +29.24<br>b = +1.18 |
| 17 4-[(7-nitro-2,1,3-benzoxadiazol-4-yl-)amino]phenol (from Example 4) | ruby-red | L = +26.70<br>a = +44.30<br>b = +18.31 |

The L*a*b* color values obtained in the foregoing examples were determined with a Chromameter II color meter supplied by Minolta. The L value stands for brightness (namely the lower the L-value the higher is the color intensity), the a-value being a measure of the red content (namely, the higher the a-value, the higher is the red content). The b-value is a measure of the blue content of the color, the blue content being the higher the more negative the b-value.

Unless otherwise indicated, the percentages given in the present application are by weight.

What is claimed is:

1. Cosmetic preparation for dyeing keratin fibers, said cosmetic preparation containing at least one 4-nitro-2,1,3-benzoxadiazole derivative of formula (I).

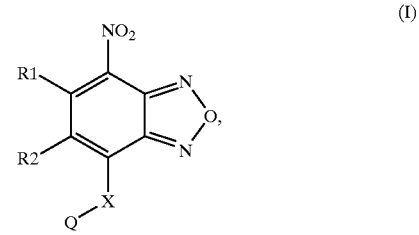

wherein

X denotes oxygen, sulfur or $NR^a$, $R^a$ standing for hydrogen, a($C_1$–C)-alkyl group, a monohydroxy-($C_1$–$C_4$)-alkyl group, a polyhydroxy-($C_2$–$C_4$)-alkyl group or a mono-($C_1$–$C_4$-alkoxy-($C_1$–$C_4$)-alkyl group, R1 and R2 can be equal or different and, independently of each other, denote hydrogen, a halogen atom, a ($C_1$–$C_4$)-alkyl group, a halogen-substituted ($C_1$–$C_4$)-alkyl group, a ($C_1$–$C_4$)-alkoxy group, a nitro group or an $NR^bR^c$ group, the $R^b$ and $R^c$ groups being equal or different and, independent of each other, denoting hydrogen, a ($C_1$–$C_4$)-alkyl group, an optionally substituted aromatic carbon ring or a ($C_1$–$C_4$)-alkane carbonyl group, or $R^b$ and $R^c$ together with a nitrogen atom forming a heterocyclic ($C_3$–$C_8$) group; and Q denotes hydrogen, an aliphatic group, an aromatic isocyclic group or an aromatic heterocyclic group;

with the proviso that, if R1, R2 and Q each denote hydrogen, then X is not oxygen.

2. Use according to claim 1, characterized in that in formula (I): Q denotes methyl, ethyl, phenyl, biphenyl, $C_6H_4R3$, $C_6H_3R3R4$ or $C_6H_2R3R4R5$, wherein R3, R4 and R5 are equal or different and, independently of each other, stand for F, Cl, Br, I, CN, $NO_2$, $CF_3$, $(C_1-C_4)$-alkyl, $(C_1-C_4)$-alkoxy, monohydroxy-$(C_1-C_4)$-alkyl, polyhydroxy-$(C_2-C_4)$-alkyl, mono-$(C_1-C_4)$-alkoxy-$(C_1-C_4)$-alkyl, $(C_1-C_4)$-alkylthio, hydroxy, $NR^dR^e$, CHO, $COR^f$, COOH, $COOR^g$, $CONHR^h$ or $NHCOR^i$ wherein $R^d$ and $R^e$, independently of each other, denote hydrogen, a $(C_1-C_4)$-alkyl group, a monohydroxy$(C_1-C_4)$-alkyl group, a polyhydroxy-$(C_2-C_4)$-alkyl group or an optionally substituted aromatic carbon ring, and $R^f$, $R^g$, $R^h$ and $R^i$, independently of each other, denote a $(C_1-C_4)$-alkyl group or an optionally substituted aromatic carbon ring.

3. Cosmetic preparation according to claim 1, wherein X denotes oxygen or $NR^a$, with $R^a$ denoting hydrogen, a $(C_1-C_4)$-alkyl group, a mono-hydroxy-$(C_1-C_4)$-alkyl group, a polyhydroxy-$(C_2-C_4)$-alkyl group or a mono-$(C_1-C_4)$-alkoxy-$(C_1-C_4)$-alkyl group;

R1=R2=hydrogen; Q stands for methyl, ethyl, phenyl, biphenyl, $C_6H_4R3$, $C_6H_3R3R4$ or $C_6H_2R3R4R5$ wherein R3, R4 and R5 are equal or different and, independently of each other stand for F, Cl, Br, I, CN, $NO_2$, $CF_3$, $(C_1-C_4)$-alkyl, $(C_1-C_4)$-alkoxy, monohydroxy-$(C_1-C_4)$-alkyl, polyhydroxy-$(C_2-C_4)$-alkyl, mono-$(C_1-C_4)$-alkoxy-$(C_1-C_4)$-alkyl, $(C_1-C_4)$-alkylthio, hydroxy, $NR^dR^e$, CHO, $COR^f$, COOH, $COOR^g$, $CONHR^h$ or $NHCOR^i$, wherein $R^d$ and $R^e$ independently of each other denote hydrogen, a $(C_1-C_4)$-alkyl group, a monohydroxy$(C_1-C_4)$-alkyl group, a polyhydroxy-$(C_2-C_4)$-alkyl group or an optionally substituted aromatic carbon ring, and $R^f$, $R^g$, $R^h$ and $R^i$ independently of each other denote a $(C_1-C_4)$-alkyl group or an optionally substituted aromatic carbon ring.

4. Cosmetic preparation according to claim 1, wherein said at least one derivative of general formula (I) is selected from the group consisting of 4-amino-7-nitro-2,1,3-benzoxadiazole; 4-N,N-dimethylamino-7-nitro-2,1,3-benzoxadiazole; 4-nitro-7-methoxy-2,1,3-benzoxadiazole; 4-nitro-7-ethoxy-2,1,3-benzoxadiazole; 4-nitro-7-phenoxy-2,1,3-benzoxadiazole; 4-nitro-7-(4'-nitrophenoxy)-2,1,3-benzoxadiazole; 4-nitro-7-(2',4',6'-trimethylphenoxy)-2,1,3-benzoxadiazole; 7-nitro-4-(N-phenylamino)-2,1,3-benzoxadiazole; 4-[N-(1-naphthalenyl)amino]-7-nitro-2,1,3-benzoxadiazole; 4-[N-(4'-chlorophenyl)amino]-7-nitro-2,1,3-benzoxadiazole; 4-[N-(4'-fluorophenyl)amino]-7-nitro-2,1,3-benzoxadiazole; 7-nitro-4-[N-(4'-nitro-phenyl)amino]-2,1,3-benzoxadiazole; 7-nitro-4-[N-(3'-nitrophenyl)-amino]-2,1,3-benzoxadiazole; 4-[N-(2',4'-dinitrophenyl)amino]-7-nitro-2,1,3-benzoxadiazole; 4-[(7-nitro-2,1,3-benzoxadiazol-4-yl)amino]benzonitrile; 4-[N-(4'-methylphenyl)amino]-7-nitro-2,1,3-benzoxadiazole; 4-[N-(2'-methylphenyl)amino]-7-nitro-2,1,3-benzoxadiazole; 4-[N-(4'-methoxyphenyl)amino]-7-nitro-2,1,3-benzoxadiazole; 4-[(7-nitro-2,1,3-benzoxadiazol-4-yl)amino]phenol; 4-[(7-nitro-2,1,3-benzoxadiazol-4-yl)amino]-3-chloro-5-nitrophenol; 3-[(7-nitro-2,1,3-benzoxadiazol-4-yl)amino]phenol; 2-[(7-nitro-2,1,3-benzoxadiazol-4-yl)amino]phenol; N-(7-nitro-2,1,3-benzoxadiazol-4-yl)-1,4-diaminobenzene; N,N-dimethyl-N'-(7-nitro-2,1,3-benzoxadiazol-4-yl)-1,4-diaminobenzene; N-(7-nitro-2,1,3-benzoxadiazol-4-yl)-2-(2'-hydroxyethyl)-1,4-diaminobenzene; N-(7-nitro-2,1,3-benzoxadiazol-4-yl)-2-(1'-hydroxyethyl)-1,4-diaminobenzene; N-(7-nitro-2,1,3-benzoxadiazol-4-yl)-2-methoxymethyl-1,4-diaminobenzene; N,N-di-(2'-hydroxyethyl)-N'-(7-nitro-2,1,3-benzoxadiazol-4-yl)-2-nitro-1,4-diaminobenzene; methyl 4-[(7-nitro-2,1,3-benzoxadiazol-4-yl)amino]benzoate; 4-nitro-7-(phenylthio)-2,1,3-benzoxadiazole; 4-[(4'-chlorophenyl)thio]-7-nitro-2,1,3-benzoxadiazole; 4-[(3'-chlorophenyl)thio]-7-nitro-2,1,3-benzoxadiazole; 4-[(4'-bromo-phenyl)thio]-7-nitro-2,1,3-benzoxadiazole; 4-[(4'-methylphenyl)thio]-7-nitro-2,1,3-benzoxadiazole; 4-[(3'-methoxyphenyl)thio]-7-nitro-2,1,3-benzoxadiazole; 4-nitro-7-[(4'-nitrophenyl)thio]-2,1,3-benzoxadiazole; 2-[(7-nitro-2,1,3-benzoxadiazol-4-yl)thio]benzoic acid; 5,7-dinitro-N-phenyl-4-amino-2,1,3-benzoxadiazole; 4-{N-[(1,1'-biphenyl)-4-yl]amino}-5,7-dinitro-2,1,3-benzoxadiazole; 4-[N-(4'-chloro-phenyl)amino]-5,7-dinitro-2,1,3-benzoxadiazole; 4-[N-(4'-bromophenyl)amino]-5,7-dinitro-2,1,3-benzoxadiazole; 4-[N-(3'-bromophenyl)amino]-5,7-dinitro-2,1,3-benzoxadiazole; 5,7-dinitro-4-[N-(4'-nitrophenyl)amino]-2,1,3-benzoxadiazole; 5,7-dinitro-4-[N-(3'-nitro-phenyl)amino]-2,1,3-benzoxadiazole; 4-[N-(4'-methoxyphenyl)amino]-5,7-dinitro-2,1,3-benzoxadiazole; 4-[N-(4'-methylphenyl)amino]-5,7-dinitro-2,1,3-benzoxadiazole; N'-(5,7-dinitro-2,1,3-benzoxadiazol-4-yl)-N,N-dimethyl-1,4-diaminobenzene; 3-[(5,7-dinitro-2,1,3-benzoxadiazol-4-yl)amino]phenol; 4-(N-methyl-N-phenylamino)-7-nitro-2,1,3-benzoxadiazole or 4-(N-ethyl-N-phenylamino-7-nitro-2,1,3-benzoxadiazole and 4-[N-(2'-hydroxyethyl)-N-[4-di-(2'-hydroxyethyl)-2-nitrophenylamino]-7-nitro-2,1,3-benzoxadiazole.

5. Cosmetic preparation according to claim 1, wherein said at least one derivative of general formula (I) is selected from the group consisting of 4-nitro-7-methoxy-2,1,3-benzoxadiazole; 4-nitro-7-ethoxy-2,1,3-benzoxadiazole; 4-nitro-7-phenoxy-2,1,3-benzoxadiazole; 7-nitro-4-(N-phenylamino)-2,1,3-benzoxadiazole; 4-[N-(4'-methylphenyl)amino]-7-nitro-2,1,3-benzoxadiazole; 4-[N-(4'-methoxyphenyl)amino]-7-nitro-2,1,3-benzoxadiazole; 4-[(7-nitro-2,1,3-benzoxadiazo-4-yl)amino]phenol; 3-[(7-nitro-2,1,3-benzoxadiazo-4-yl)amino]phenol; 2-[(7-nitro-2, 1,3-benzoxadiazol-4-yl)amino]phenol; 4-[(7-nitro-2,1,3-benzoxadiazol-4-yl)amino]-3-chloro-5-nitrophenol; N-(7-nitro-2,1,3-benzoxadiazol-4-yl)-1,4-diaminobenzene; N-(7-nitro-2,1,3-benzoxadiazol-4-yl)-2-(2'-hydroxyethyl)-1,4-diaminobenzene; N-(7-nitro-2,1,3-benzoxadiazol-4-yl)-2-(1'-hydroxyethyl)-1,4-diaminobenzene; N-(7-nitro-2,1,3-benzoxadiazol-4-yl)-2-(methoxymethyl)-1,4-diaminobenzene; N,N-dimethyl-N'-(7-nitro-2,1,3-benzoxadiazol-4-yl)-1,4-diaminobenzene; N,N-di-(2'-hydroxyethyl)-N'-(7-nitro-2,1,3-benzoxadiazol-4-yl)-2-nitro-1,4-diaminobenzene and 4-[N-(2'-hydroxy-ethyl-N-[4-di-(2'-hydroxy-ethyl)-2-nitrophenylamino]-7-nitro-2,1,3-benzoxadiazole.

6. Cosmetic preparation according to claim 1, and containing said at least one 4-nitro-2,1,3-benzoxadiazole derivative of general formula (I) in an amount from 0.01 to 10 wt. %.

7. Cosmetic preparation according to claim 1, further comprising at least one known direct dye from the group consisting of anionic or cationic dyes, nitro dyes, azo dyes, anthraquinone dyes, triphenylmethane dyes or disperse dyes.

8. Cosmetic preparation according to claims 1 or 7, in the form of a shade fixative or color fixative and further comprising at least one natural or synthetic polymer or at least one modified polymer of natural origin.

9. Cosmetic preparation according to claim 1, further comprising an oxidation dye precursor.

10. Cosmetic preparation according to claims 1 to 9, further comprising an oxidant mixed with said at least one 4-nitro-2,1,3-benzoxadiazole derivative.

11. Cosmetic preparation according to claims 1 to 10, consisting of a hair colorant composition.

* * * * *